United States Patent [19]

Davis

[11] Patent Number: 5,429,620
[45] Date of Patent: Jul. 4, 1995

[54] CALIBRATED DISCONNECT JOINT FOR URETHRAL CATHETER

[75] Inventor: Richard C. Davis, Palm Harbor, Fla.

[73] Assignee: Uroquest Corporation, Tampa, Fla.

[21] Appl. No.: 283,157

[22] Filed: Aug. 3, 1994

[51] Int. Cl.⁶ .............................................. A61M 3/00
[52] U.S. Cl. .................................... 604/283; 604/905
[58] Field of Search .......... 604/283, 284, 96, 240-243, 604/264, 905, 93, 174, 175

[56] References Cited

U.S. PATENT DOCUMENTS

| | | |
|---|---|---|
| 3,769,981 | 11/1973 | McWhorter . |
| 4,140,127 | 2/1979 | Cianci et al. . |
| 4,155,364 | 5/1979 | Boxer . |
| 4,187,846 | 2/1980 | Lolachi et al. . |
| 4,270,534 | 6/1981 | Adams . |
| 4,701,162 | 10/1987 | Rosenberg . |
| 4,878,900 | 11/1989 | Sundt . |
| 5,057,093 | 10/1991 | Clegg et al. ............... 604/905 X |
| 5,092,854 | 3/1992 | Black . |
| 5,263,945 | 11/1993 | Byrnes et al. .................. 604/283 |
| 5,267,983 | 12/1993 | Oilschlager et al. ............. 604/283 |
| 5,284,134 | 2/1994 | Vaughn et al. ................ 604/283 X |

Primary Examiner—John D. Yasko
Attorney, Agent, or Firm—Griffin, Butler Whisenhunt & Kurtossy

[57] ABSTRACT

A calibrated disconnect joint for use with indwelling urethral balloon catheters is included between main portions of a catheter-drainage tube (10) and a bag-drainage tube (16). The calibrated disconnect joint includes male and female portions (or tubularly-shaped wall members) (54, 60; 70, 72; 90, 92; 110, 112) with one of these being a ribbed portion and the other being a grooved portion. If a tension of between ½ pound and 4 pounds, preferably between 2½ and 3 pounds, is applied to the calibrated disconnect joint, the ribbed and grooved portions separate from one another to allow the main portions of the catheter-drainage and bag-drainage tubes to separate. Valves (86, 88) which automatically close their respective lumens upon separation are included on each of the ribbed and grooved portions so that upon separation little or no fluid escapes and there is a barrier to bacteria invasion.

25 Claims, 4 Drawing Sheets

CALIBRATED DISCONNECT JOINT FOR URETHRAL CATHETER

BACKGROUND OF THE INVENTION

This invention relates broadly to the art of Foley-type urethral drainage catheters, and more particularly to safety mechanisms for use with such catheters.

Voluntary control over discharge of bladder contents is a serious and distressing problem for persons whose natural anatomy is no longer capable of completely controlling the outflow of urine from the bladder for such reasons as advanced age, surgery, disease, trauma, denervation, and other malformation of the natural lower urinary tract.

A traditional urethral balloon catheter of a well-known type comprises a flexible catheter tube which extends from outside the body along the urethra and into the bladder. The catheter tube comprises a main lumen for passage of urine and a much smaller lumen leading to an annular expandable balloon, which is adjacent the distal end of the catheter and which can be expanded within the bladder by pumping a fluid along the smaller lumen to thereby prevent accidental retraction of the catheter from the urethra. Typically in such a system, urine continuously drains through the catheter main lumen which is, in turn, connected to a length of drainage tubing and finally a drainage bag worn by, or at least maintained near, the patient.

Although urethral catheters of the type described above are quite beneficial and solve many problems, they also create other problems. For example, such a catheter main lumen which extends from outside the body into the body provides a path along which, if one is not careful, bacteria can enter, or invade, the body. For this reason, it is common for urethral catheter systems to be constructed and used as "closed systems". That is, it is desirable that the flexible, internal, catheter-drainage tubes have sealed connections with the exterior drainage tubes leading to the bags worn by the patients so that they cannot be easily separated (which would allow bacteria to invade the lumen and migrate into the body). Thus, it is an object of this invention to provide a normally "closed system" indwelling urethral catheter system.

Yet another problem which is encountered with indwelling urethral catheters is that externally extending tubes thereof can accidentally snag on surrounding objects. Similarly, agitated, demented, disoriented, and/or otherwise confused patients can pull on externally extending tubes voluntarily. Such stresses on the external tube are transmitted to the internal tubes and balloons and can be disastrous for such patients, especially if extirpation (defined as the forceful and traumatic withdrawal of a Foley-type urinary catheter through the urethra while the bladder-retaining balloon is still inflated) ensues which can cause frank hematuria, urethral lacerations, stricture formation, infections, prostatitis, impotence, etc. For example, if a patient wearing such an indwelling urethral catheter system were being "wheeled" through the hospital on a heavy hospital bed and the external tubing should catch on a stationary structure, axial tension would be exerted along the tube to the balloon which is located in the patient's bladder. The balloon, now held taut against the bladder neck and sphincter, exerts a resistance, or stress, on the tube which, under a continual load, causes the tube to stretch. Since a standard catheter tube is relatively elastic, it will stretch to almost one and one half times its normal length before it begins to exert a deforming force on the balloon. Eventually,-however, the balloon will deform getting thinner at its connection to the tube, and when sufficient force is applied, it will be pulled out of the bladder and along the urethra, typically causing lacerations or ruptures of the urethra and/or sphincter muscle. If the balloon is of such a size or this force too great, the catheter tube may break. When this occurs, the distal portion of the catheter next to the balloon is retained inside the patient's bladder. It is then necessary to use a cystoscope to remove those portions of the balloon catheter system remaining in the patient's body.

The incidence of extirpation varies widely. It is more common in extended-care facilities, for wheelchair-bound patients, and increases where the care-giver's skill level decreases. The level of occurrence would have to be classified as unusual, but not rare, since nearly every health-care provider has personally witnessed and/or treated this problem. When extirpation occurs, factors which will affect the degree of damage caused thereby are the amount of fluid in the balloon, the balloon size, the type of catheter material (latex versus silicon), the force applied to the catheter (a gentle continuous force normally is less damaging than a rapidly applied force), and pre-existing anatomic conditions of the patients (enlarged prostate, spastic bladder, scarring, radiation, etc.). Normally, latex balloons tend to more easily deform than silicone balloons and therefore cause less damage than do the more rigid silicone balloons.

When the catheter tube is first stretched, as described above, the patient feels discomfort and therefore usually realizes that there is a problem and takes action to solve the problem. However, this is not always possible. Thus, it is an object of this invention to provide a urethral catheter system which has a safety mechanism for protecting the patient from undue tension placed on external tubes of urethral catheter systems.

Catheter-drainage tubes of prior art urethral catheter systems normally contain a forked external section, with one branch of the fork defining the main drainage lumen and the other branch of the fork (the inflation pigtail) defining the balloon-inflating lumen of the balloon. The branch defining the main lumen normally includes, integral and as one part therewith, an enlarged female terminal funnel portion for receiving a male connector of an external bag-drainage tube. The male connector of the bag-drainage tube has a long tapered external surface which mates in a tight-press fit with a relatively long internal surface of the enlarged female terminal funnel portion. This press fit contains a large surface area of contact to ensure that the connection remains sealed against bacterial invasion and that these members do not easily separate. To further ensure that there is no leakage or separation commercially available systems commonly tape this connector junction. If the catheter bag/system is purchased as separate components, nurses quite frequently place tape at the connecting edges between the elongated female terminal funnel portion of the catheter-drainage tube and the male connector of the bag-drainage tube. However, this not only prevents bacteria migration and ensures that there is no separation, but it also ensures that, should the external tubing become snagged, an undue amount of axial force will be applied to the balloon which can cause severe injury to the patient, as mentioned above.

Thus, it is another object of this invention to provide a connection between a catheter-drainage tube and a bag-drainage tube which ensures that there is no leakage or separation under normal circumstances, but which, in a calibrated manner, does allow separation if an excessive axial force is applied to external tubes of a urethral catheter "closed system."

Yet another problem, related to those already discussed for urethral catheter systems, is that if there is a separation between the bag-drainage tube and the catheter-drainage tube, or if either of these two tubes breaks, not only will bacteria be allowed to invade the system, and therefore enter the patient, but also foul-smelling and possibly contaminated urine will be released which is unsanitary to surroundings, disagreeable and potentially dangerous to workers, and highly embarrassing to the patient. Thus, it is another object of this invention to provide a urethral catheter system which automatically separates in a calibrated manner upon the application of an excessive axial force above a particular threshold tension thereto, but which, when it does separate, prevents escape of fluid and migration of bacteria.

It is yet another object of this invention to provide a urethral catheter system which not only protects the patient and surroundings, as mentioned above, but which is also not unduly expensive.

SUMMARY

According to principles of this invention, a calibrated disconnect joint is included in a Foley-type urethral catheter "closed system" located between main portions of the catheter-drainage tube and the bag-drainage tube. The calibrated disconnect joint includes male and female portions with one of these being a ribbed portion, having an extending annular rib on a surface thereof, and the other being a grooved portion, having an annular groove for receiving the annular rib. If a tension of between ½ pound and 4 pounds, preferably between 2½ and 3 pounds, is applied to the calibrated disconnect joint, the ribbed and grooved portions thereof separate to allow the main portions of the catheter-drainage and bag-drainage tubes to separate. Valves, which automatically close their respective lumens upon separation, are included on each of the ribbed and grooved portions so that upon separation there is little or no fluid escape and little bacteria invasion into either tube end.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

BRIEF DESCRIPTION OF THE PREFERRED EMBODIMENT

Figure 1:
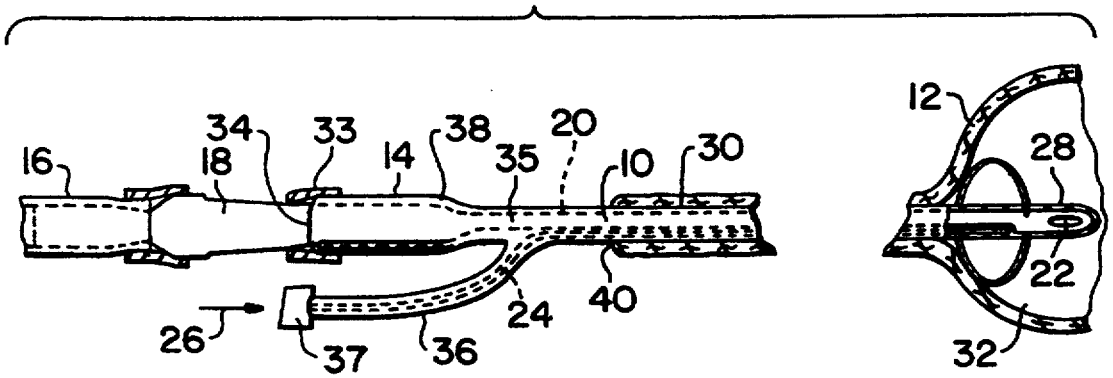
FIG. 1 is a segmented, partially cutaway, side view of a prior art urethral catheter system.

Looking first at the prior art Foley, or balloon, urethral catheter system of FIG. 1, this system includes a catheter-drainage tube 10 having a balloon 12 at a distal end thereof and an enlarged terminal funnel portion 14 at a proximal end thereof and a bag-drainage tube 16 with an attached connector 18 for removably attaching the bag-drainage tube 16 to the enlarged terminal funnel portion 14 of the catheter-drainage tube 10. The catheter-drainage tube 10 defines a main lumen 20 through which urine from apertures 22 at the distal end flows. The urine eventually flows into a bag (not shown) attached to the bag-drainage tube 16. The catheter-drainage tube 10 also includes a balloon-inflation lumen 24 which is used to inflate the balloon 12 by fluid injected through a check valve 37 at arrow 26.

The prior-art urethral catheter of FIG. 1 is basically used as follows. The catheter-drainage tube 10, with its attached balloon 12 and enlarged terminal funnel portion 14, is removed from a sterile package and the distal tip 28 thereof is inserted into a urethra 30 until the deflated balloon 12 is positioned in the interior of a bladder 32. At this point, an inflation fluid is injected through the check valve 37 into the balloon-inflation lumen 24 to inflate the balloon 12 so that the catheter-drainage tube 10 will remain in position with the enlarged terminal funnel portion 14 being located externally of the body and the inflated balloon 12 internally of the body. In many cases the catheter's terminal funnel portion 14 is pre-packaged while it is inseparably connected to the drainage tubing adaptor 18 via shrink-wrap taping 33, or some other connecting method. However, for those cases where the catheter is packaged separately from the drainage tube/bag system, the bag-drainage tube 16, which is integral with a drainage bag (not shown), along with its connector 18, is removed from its separate packaging and the male connector 18 thereof is then shoved into the enlarged terminal funnel portion 14 so that there is sufficient external and internal surface contact between these two members to prevent bacterial migration therebetween and so that these two members are held tightly together and cannot be inadvertently separated. In this regard, quite often nurses place tape 33 at the interface 34 between these two members to ensure that there is no separation and no bacterial migration. Further, the connector 18 is usually of PVC which tends to stick to enlarged terminal funnel portion 14, which is often of latex, over a period of time. It should be noted that distal, or upstream, of the enlarged terminal funnel portion 14 there is a fork 35 in the catheter-drainage tube 10, with the balloon-inflation lumen 24 following one branch 36 of this fork and the main lumen 20 following the other branch 38 of this fork. The length of the catheter-drainage tube 10 is designed so that the fork 35 is located distal to the entrance area 40 of the body of the patient.

As mentioned above, a significant problem with the prior-art system of FIG. 1 is that if an undue stress is applied to the bag-drainage tube 16, this stress is transmitted along the catheter-drainage tube 10 to the balloon 12 and will eventually injure the bladder, the urethra, and related parts.

Figure 2:
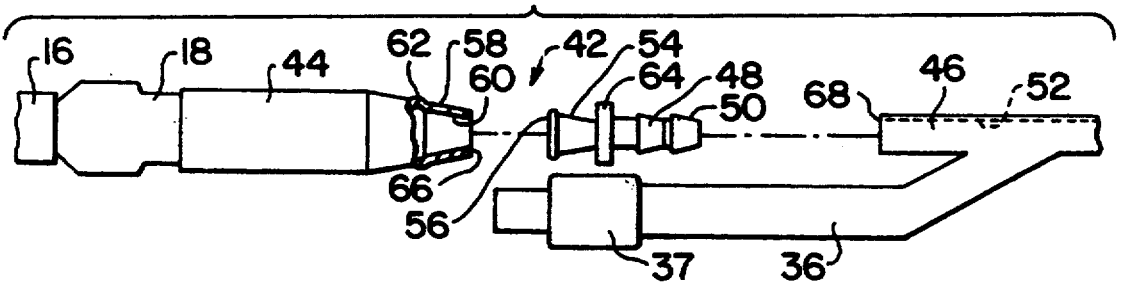
FIG. 2 is an exploded, partially cutaway, segmented, side view of a urethral catheter system having a disconnect joint of this invention.

Looking now at a urethral catheter system 42 of this invention, which is shown in FIG. 2, the enlarged terminal funnel portion 14 of FIG. 1 is replaced by a drainage tubing adaptor (tubularly-shaped wall member) 44 which is attached to the rest of the catheter-drainage tube 46 by means of a male/male connector (tubularly-shaped wall member) 48. The catheter-drainage tube 46 can be a specialized drainage tube or it can be a currently off-the-shelf drainage tube with the enlarged terminal funnel portion 14 cut off. In any event, the drainage tubing adaptor 44 and the male/male connector 48 form a calibrated disconnect joint between the catheter-drainage tube 46 and the bag-drainage tube 16. In this regard, at the distal end thereof the male/male connector 48 has a dual-barb external surface 50 for being shoved into the main lumen 52 of the catheter-drainage tube 46 to form a substantially permanent connection therewith. It would take an extremely strong force to pull these members apart and, in any event, a greater force than 6 pounds. However, at the proximal end of the male/male connector 48 is a conically-shaped outer surface 54 with a concentric, annularly-shaped protruding rib 56 at an outer end thereof. In this respect, the conically-shaped outer surface 54 flares outwardly, away from the catheter-drainage tube 46 toward the annularly-shaped protruding rib 56.

The drainage tube adaptor 44, on the other hand, at a distal end portion 58 thereof, has an internal surface 60 which is also conically sized and shaped to have approximately the same size and shape as the conically-shaped outer surface 54 of the proximal end of the male/male connector 48; although it may be slightly smaller. Similarly, the internal surface 60 includes an annularly-shaped notch 62 for receiving the annularly-shaped protruding rib 56. Thus, when the conically-shaped outer surface 54 of the proximal end of the male/male connector 48 is positioned inside the internal surface 60 of the drainage tubing adaptor 44, these members have surface contact all along the common length thereof and there is a calibrated engagement between the annularly-shaped protruding rib 56 and the annularly-shaped notch 62. In this respect, the drainage tubing adaptor 44 is constructed of latex or silicon whereas the male/male connector 48 is constructed of medical grade polyethylene and has an external surface which is quite smooth and slippery. Thus, the drainage tubing adaptor 44 tends not to stick to the male/male connector 44, but rather its engagement therewith is substantially determined by the mechanical interconnection between these two parts and the durometer hardness of the materials.

Figure 3:
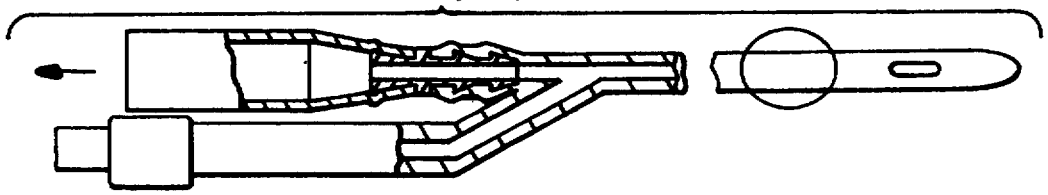
FIG. 3 is a view similar to FIG. 2, but showing the disconnect joint assembled rather than being exploded and not including a bag-drainage tube and connector.

In the embodiment of FIGS. 2 and 3, the male/male connector 48 has a separator disk 64 formed as part thereof to impinge on ends 66 and 68 of the respective drainage tubing adaptor 44 and the catheter-drainage tube 46 when the system is assembled as depicted in FIG. 3.

By properly choosing the materials and sizing the conically-shaped outer surface 54, the annularly-shaped protruding rib 56, the internal surface 60, and the annularly-shaped notch 62, it is possible to achieve a calibrated disconnect (or frangible) joint with the drainage tubing adaptor 44 separating from the male/male connector 48 at an axial stress optimally between 2½ and 3 pounds. It is preferable that this separating axial stress remain below 4 pounds at all times but in no event should it be above 6 pounds.

Figure 4:
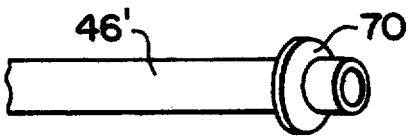
FIG. 4 is an isometric view of a ribbed portion of a second embodiment disconnect joint of this invention made as part of a catheter-drainage tube.
Figure 5:
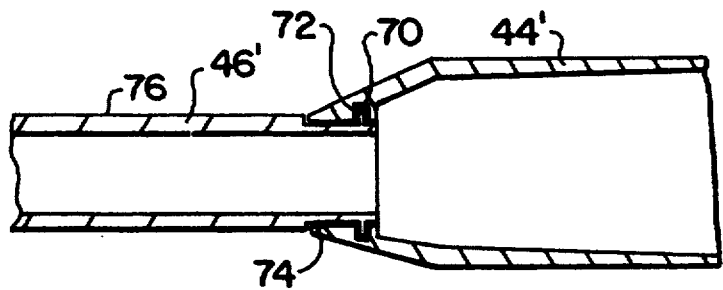
FIG. 5 is a segmented, cross-sectional, side view of an assembled disconnect joint using the component of FIG. 4.

Looking now at the FIGS. 4 and 5 embodiment, in this embodiment, a specialized catheter-drainage tube 46' has formed integral therewith a radial, outwardly-extending, disk 70 which mates with an internal annular groove 72 in a drainage tubing adaptor 44'. In the FIG. 5 embodiment, that portion 74 of an external surface 76 of the catheter-drainage tube 46' where the radially, outwardly-extending disk 70 is located, is indented from the rest of the external surface 76, however, this is not essential.

In any event, the sizes, shapes, and materials of the elements forming the FIGS. 4 and 5 calibrated disconnect joint are such as to allow separation between the catheter-drainage tube 46' and the drainage tubing adaptor 44' if an axially separating pull is applied thereto of between 2½ and 3 pounds.

Describing next use of the urethral catheter systems depicted in FIGS. 2-5, the catheter-drainage tube 46, the male/male connector 48 and the drainage tubing adaptor 44 can all be packaged in sterile packaging together or the connector 48 and adaptor 44 can be together in a package separate from that of the catheter-drainage tube. If they are all packaged together, these elements are taken out of the packaging in an already assembled state and are administered to a patient as described above in relation to the prior-art system of FIG. 1. Thereafter, as in the prior art, the connector 18 of the bag-drainage tube 16 is removed from its separate packaging and attached to the drainage tubing adaptor 44.

Similarly, in the FIGS. 4 and 5 embodiment, the catheter-drainage tube 46' and the drainage tubing adaptor 44' are packaged in an assembled condition (as shown in FIG. 5) and are administered to a patient in this assembled condition. Also, as in the FIGS. 2 and 3 embodiment, once the system is in a patient, the connector 18 of the bag-drainage tube 16, after being removed from its separate packaging, is attached to the drainage tubing adaptor 44'.

In both the FIGS. 2 and 3 and FIGS. 4 and 5 systems, if an external stress force is applied to the bag-drainage tube 16, the catheter-drainage tube 46 (or 46') will first stretch, as in the prior art. However, if the stress force continues to increase, eventually reaching a magnitude of approximately between 2½ and 3 pounds, the grooved drainage tubing adaptor 44 (or 44') will disengage from the ribbed connector (56 or 70). That is, looking at FIGS. 2 and 3, the internal surface 60 with the annularly-shaped groove, or notch, 62 will disengage from the conically-shaped outer surface 54 and the annularly-shaped protruding rib 56 when a separating force of approximately between 2½ and 3 pounds is applied between these two members. Thus, no force will ever be applied to the balloon 12 greater than approximately 3 pounds to cause serious injury to the patient.

It will be appreciated by those of ordinary skill in the art that having a calibrated disconnect joint which will not disconnect until a force greater than approximately 2½ pounds is applied thereto will ensure that there is not a premature disconnection caused by usual activities of the patient. For example, if a bag attached to the bag-drainage tube 16 has ½ gallon of fluid therein and the bag is inadvertently dropped, it should not create a force greater than 2½ pounds and should therefore not cause a disconnect of the disconnect joint of this invention.

A further advantage of this invention is that, in the FIGS. 2 and 3 embodiment, there is so much contact between the internal surface 60 of the drainage tubing adaptor 44 and the conically-shaped outer surface 54 of the male/male connector 44 that bacterial migration is prevented. That is, the connection between the drainage tubing adaptor 44 and the male/male connector 48 is designed to be bacteria-migration-free. Similar comments also apply to the FIGS. 4 and 5 embodiment.

Yet another benefit of this invention is that it limits the amount of force which will be applied to a balloon in a bladder to less than approximately 3 pounds. In this regard, when a pull on a catheter-drainage tube is less than three pounds, the balloon is not unduly deformed and therefore does not cause injury to the patient. Actually, serious injury to a patient is usually caused at around 6–8 pounds of pull on the catheter-drainage tube; thus, the disconnect joint of this invention provides a margin of error for protecting the patient.

While the invention has been particularly shown and described with reference to a simplified embodiment, it will be understood by those of ordinary skill in the art that various changes in form and detail may be made therein without departing from the spirit and scope of the invention.

Figure 6:
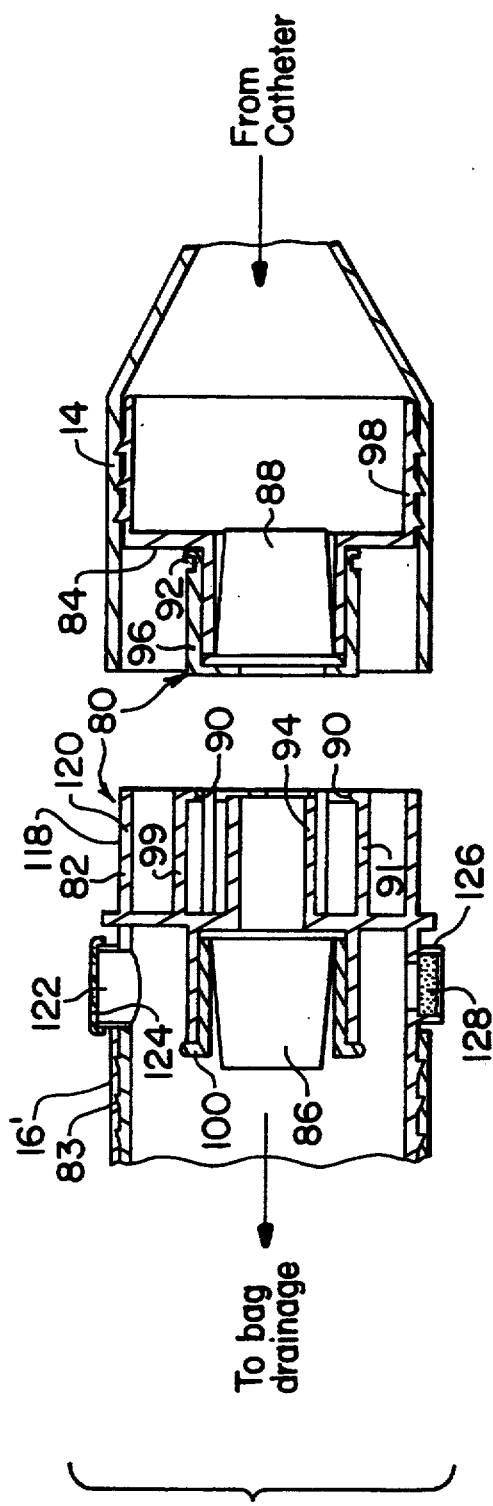
FIG. 6 is an exploded, segmented, partially cross-sectional, side view of a urethral catheter system having a disconnect joint of this invention in an embodiment which also includes automatic disconnect valves on both ribbed and grooved portions of a calibrated disconnect joint.

For example, with reference to FIG. 6, a disconnect joint 80 of this invention comprises a female cylindrical ribbed member 82 which is strongly attached to a bag-drainage tube 16' by means of barbs 83 and a male grooved member 84 which is strongly, or permanently, attached to the enlarged terminal funnel portion 14 of a catheter-drainage tube (most of which is not shown). In this regard, the disconnect joint 80 is constructed of a rather stiff or rigid plastic and can be packaged and distributed with the bag-drainage tube 16', the catheter-drainage tube 10, or by itself. In any event, each of the ribbed and grooved members 82 and 84 has a duckbill valve 86 and 88 mounted therein. In this regard, other types of check valves could also be used. The duckbill valve 86 naturally allows fluid to flow from upstream to downstream (distal-to-proximal), that is, from the bladder to the drainage bag, whereas the duckbill valve 88 naturally allows upstream (proximal-to distal) flow, that is from the drainage bag towards the bladder. However, when the ribbed member 82 is mated with the grooved member 84, so that ribs 90 on a circular artery of flexible cantilever arms 91 engage an annular groove 92, a tubularly-shaped valve opener 94 of the ribbed member 82 is inserted into the duckbill valve 88 to hold the duckbill valve 88 open. Thus, fluid can continually flow downstream from the bladder towards the drainage bag through the duckbill valve 88 so long as the ribbed and grooved members 82 and 84 are interconnected. Of course, the duckbill valve 86 always allows flow from the bladder toward the drainage bag.

As in the other embodiments, the ribbed and grooved members 82 and 84 are designed so that they will separate at a tension force of between 2½ and 3 pounds. Thus, if a patient is wearing a urethral catheter system having the disconnect joint 80 of FIG. 6 mounted thereon, and if external tubing thereof snags an external body to apply an internal force greater than a calibrated force of between around 2½ to 3 pounds on the catheter and balloon, the ribbed and grooved members 82 and 84 separate and the tubular valve opener 94 is pulled out of the duckbill valve 88. Thereafter, fluid cannot flow out of the duckbill valve 88 nor can it flow upstream out of the duckbill valve 86, thus, not only has the catheter-drainage tube separated from the bag-drainage tube at a calibrated tension in order to protect the patient, but it has separated at a point where there are valves to prevent fluid from flowing out of the bag-drainage and catheter-drainage tubes. It will be understood by those of ordinary skill in the art that this valved feature of the calibrated disconnect joint not only makes operation of the disconnect joint more sanitary, but also gives confidence to the patient and to hospital personnel. An interesting feature of the FIG. 6 embodiment is that the groove 92 is defined by a valve keeper 96 which is permanently attached to a main housing 98 for holding the duckbill valve 88 on the main housing 98. The ribs 90 on the flexible cantilever arms 91 ribbed member 82, on the other hand, are on a separate member 99 from a valve keeper 100. It is also interesting that in the FIG. 6 embodiment the groove 92 is on the male member, whereas the ribs 90 are on the female member. As in the other embodiments, an important feature of this embodiment is that there is separation between main portions of the catheter-drainage tube and the bag-drainage tube at a tension of between approximately 2½ and 3 pounds.

With regard to the tension, or separation force, necessary for separating members of the calibrated disconnect joint of this invention, standard urinary catheters come in many French sizes, with 16 and 18 being the most common in commercial use. Pull tests have shown that forces required to extirpate 5 cc latex balloons of 16 French latex averaged 7.25 pounds of axial traction force applied over 0.5 seconds. 30 cc silicon balloons in 22 French 22 silicon catheters required 25 pounds of axial traction applied over 0.5 seconds before extirpation occurred. From this data, it has been determined that the calibrated disconnect joint should certainly separate with a load of something less than 7.25 pounds.

Furthermore, it has been determined that the calibrated disconnect joint should not separate at too low a tension, because premature separation would be inconvenient, and could possibly cause leakage of urine, increased potential for bacterial invasion, and the necessity of implanting a new catheter system, depending upon the embodiment used. Thus, a calibrated disconnect joint of this invention can fail: a) by not releasing when a sufficient force is present, b) by releasing too early upon the application of a very small force, or c) by allowing the invasion of bacteria into the system with no release. Thereby, it has been determined that an acceptable tension force release range would be between ½ pound and 6 pounds, but that an optimal tension release range would be approximately 2½ to 3 pounds of axial traction. At a 3 pound axial traction, a 16 French Bard latex Foley catheter was stretched to 150% of its original length and was applying in excess of 20 cm of water pressure (the capillary filing pressure) to the bladder balloon.

Since the calibrated disconnect joint must be impenetrable to bacteria, it is required that an interference fit between the ribbed and grooved members provide an interference press-fit of greater than 50% of a standard IV-catheter luer fit. Such surface interference requires a certain amount of force by itself to separate and, by calculating backwardly therefrom, it has been determined that a force of approximately 2½ pounds allows for the appropriate minimum axial force required for separation.

Defining the release force at 2.5 pounds therefore allows a maximum release force of 3 pounds if a durometer variance is maximized to +2.0 durometer and an internal recess is reduced by 0.005" and the annular rib is increased by 0.005". All of these factors could work to increase the separation force.

When these factors are minimized, a release force of 2 pounds is calculated which is acceptable as a lower limit. Such a release force would be the equivalent of dropping a drainage bag with 600 cc of urine without causing a connector separation.

Yet another beneficial feature of the FIG. 6 embodiment is that the flexible cantilever arm 91 with ribs 90 and the groove 92 are internal of contacts between the enlarged terminal funnel portion 14 of the catheter-drainage tube and an outer surface 118 of an outer housing portion 120 of the ribbed member 82. The surface contact between the enlarged terminal funnel portion 14 and the outer housing portion 120 is sufficiently great to prevent bacterial penetration, thus, it is not necessary that the annular cantilever arms 91 be solid. That is, the annular cantilever arms 91 can be separated by axial slits to provide radial spring thereto without fear of "breaking" a bacterial seal.

Although the ribbed member 82 is shown in FIG. 6 as being attached to a modified bag-drainage tube 16', it would be possible to design the outer housing portion 120 of the ribbed member 82 so that the barbs 83 will fit a standard bag-drainage tube 16 (shown in FIG. 1).

Along these lines, it is possible to create a urethral catheter having a calibrated disconnect joint of this invention "from scratch", however, it is also possible to design a system, such as the disconnect joint 80 shown in FIG. 6, for existing urethral catheter systems.

It would also be possible to design the valve keepers 96 and 100 to be the same size so that these members could be interchangeable.

Similarly, although the valves 86 and 88 in the FIG. 6 embodiment are duck-bill valves, these valves could be other one-way valves such as ball-check valves, umbrella valves, etc. The one-way valve on the catheter drainage tube side is oriented against urine flow. When any of these valves are used, those of ordinary skill in the art will realize that valve openers of appropriate configurations can also be used for holding them open.

Figure 7:
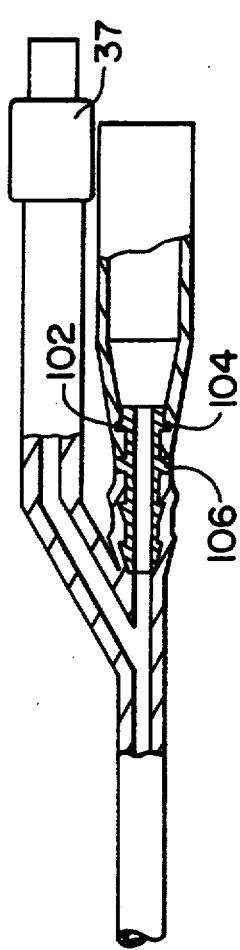
FIG. 7 is a segmented, partially cutaway, side view of a urethral catheter system having a disconnect joint assembly which is similar to, but slightly different than that shown in FIGS. 2 and 3.

The FIG. 7 embodiment is quite similar to the FIG. 2 embodiment with the exception that a protruding rib 102 and its counterpart annular groove 104 are not positioned at a proximal end of a male/male connector 106, as it is shown in FIG. 3.

Figure 8:
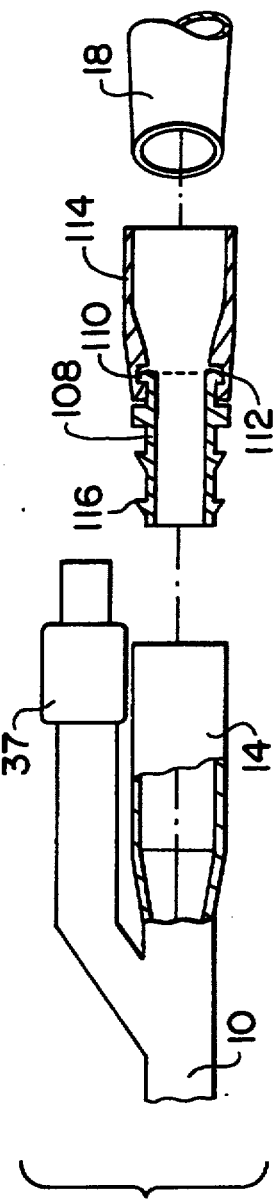
FIG. 8 is an exploded, segmented, partially cutaway, partially cross-sectional, side view of a urethral catheter system having a disconnect joint of this invention in which both the rib and groove portions of the disconnect joint are separate from a catheter-drainage tube and a bag-drainage tube.

In the FIG. 8 embodiment, a male/male connector 108 has an annular rib 110 thereon which mates with an annular groove 112 on a specialized drainage tubing adaptor 114 which, in turn, mates with a normal connector 18 of a bag-drainage tube 16 (see FIG. 1 for element 16). The male/male connector 108, in this case, has barbs 116 for substantially permanently attaching the male/male connector 108 to a normal, enlarged terminal funnel portion 14 of a catheter drainage tube 10.

Finally, in a first embellishment of the FIG. 6 embodiment, the outer housing portion 120 of the ribbed member 82 of the disconnect joint 80 further includes a sampling/injection port 122 which is commonly incorporated into many male connectors of conventional bag-drainage tubes. Such a sampling/injection port comprises a circular latex membrane 124 which is incorporated into the outer housing portion 120. In this regard, many prior art systems include similar circular latex membranes incorporated into housings of male connectors. This membrane is readily punctured by needles and other such objects for the purpose of instilling or withdrawing fluids into or from the closed drainage system without disconnecting the tubing. The latex membrane automatically closes upon removal of a needle.

A second additional embellishment includes the incorporation of a venting assembly 126. The venting assembly comprises a semi-permeable porous hydrophobic filter device 128 including parts integrally molded into the outer housing portion 120 of the FIG. 6 embodiment. This vent allows air to be filtered and then enter the closed drainage assembly to facilitate the flow of urine down the drainage tube from the bladder, thereby preventing suction which can occur along an unvented tubing. The semi-permeable filter 128 does not allow escape of liquids.

Figure 9:
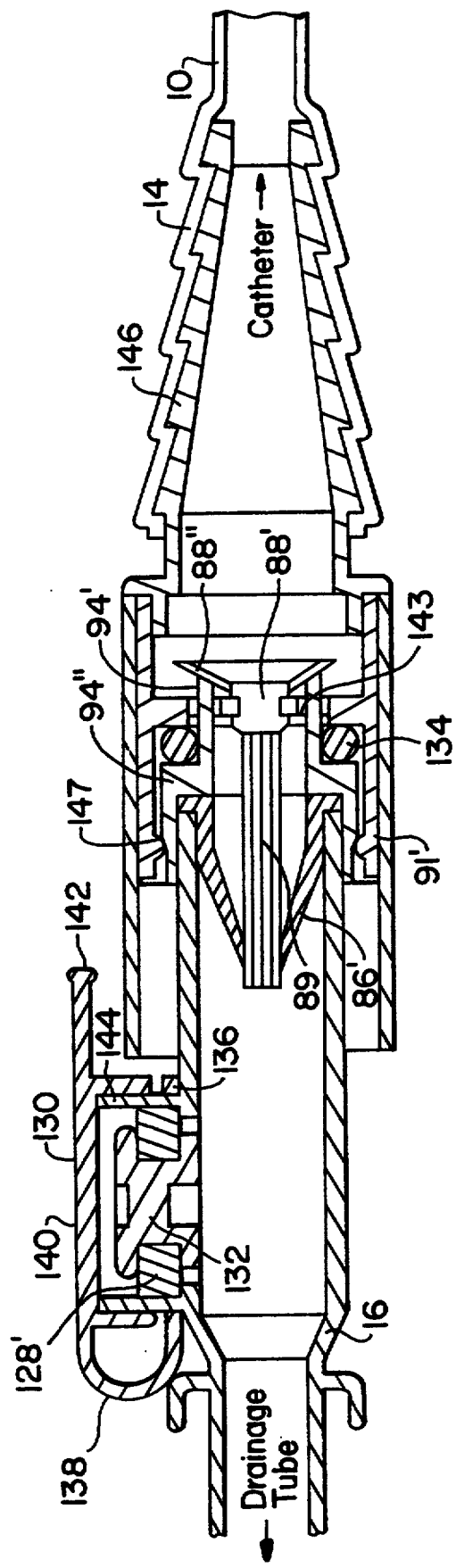
FIG. 9 is a partially cross-sectional, side view of a preferred urethral catheter system having a disconnect joint of this invention in an embodiment which also includes automatic disconnect valves on both ribbed and grooved portions of the calibrated disconnect joint.
Figure 10:
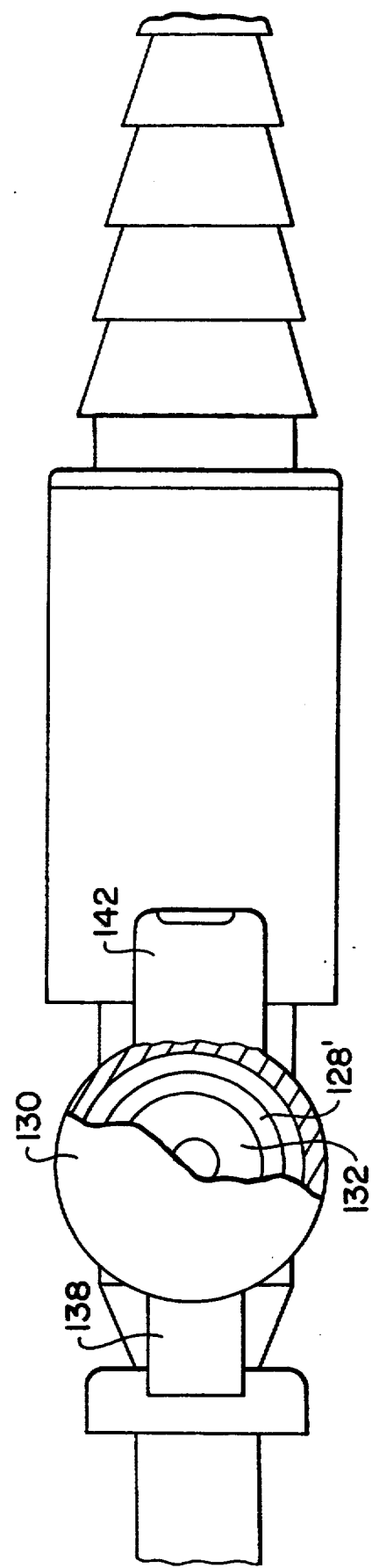
FIG. 10 is a partially cutaway top view of the urethral catheter system of FIG. 9.

The presently preferred embodiment of this invention, as shown in FIGS. 9 and 10, includes a combination of salient features of the preceding embodiments, with several additional enhancements. First, there is the addition of a fluid-impervious polyethylene plastic cap 130 which comprises an integral retaining ring 136 at its base having a flexible lid strap 138 connected to the lid 140. The lid has an integral overhang 142 which is used to easily pop the lid off of the molded-in cap flange 144. The cap 130 sealingly press-fits onto this flange 144 thereby selectively preventing any egress of fluids or ingress of bacteria through a filter 128' and a plug membrane 132 into the "closed system".

Within the flange 144 is mounted the redesigned hydrophobic filter 128' which is annular in shape and has a hollow center, thereby being shaped like a donut. In the center of the filter 128' is mounted the latex plug membrane 132 which replaces the separately mounted latex cap 124 of the FIG. 6 embodiment. Thus, this arrangement allows a universally-selective fluid exchange between outside atmosphere and the interior of the drainage tube 16.

A valving assembly comprises a duckbill valve 86' similar to that of the previous descriptions. However, in this preferred embodiment the duckbill valve 86' is stinted open by a splined shaft 89 of an umbrella valve assembly 88', which replaces the duckbill valve 88 of the FIG. 6 embodiment.

This umbrella valve assembly 88' is press fitted into place in a web-work structure 143 of a spring clamp assembly 91' which allows passage therethrough of valve opener risers 94' of a riser assembly 94", which risers 94' lift valve leaflets 88" of the umbrella valve assembly 88', thereby permitting unrestrained passage of urine therethrough. By stinting open the duckbill valve 86' urine is allowed to drain easily through the space around the splined shaft 89 into the of the lumen of the bag drainage tube 16, thereby reducing collection of urine in this space. Another additional feature is a sealing "O" ring 134 which prevents passage of urine into a space between the riser assembly 94" and the spring clamp assembly 91'. Each of these enhancements acts together to reduce the potential for pooling and/or collection of any residual urine in these small spaces within the device, to reduce both the potential for spillage upon separation, as well as the potential for infection.

In operation, a coupling 146 is attached at its right end (FIG. 9) to a coupling 14 of a catheter drainage tube 10. The spring clamp assembly 91' is permanently affixed to the coupling 146 and the web-work structure 146 of the spring clamp assembly 91' holds the umbrella valve assembly 88' concentric therewith for controlling flow of fluid through the web-work structure 143.

The riser assembly 94" and the duckbill valve assembly 86', on the other hand, are affixed to the bag drainage tube 16.

The riser assembly 94" and the spring clamp assembly 91' interengage with one another at engaging points 147 such that if a tension of between ½ lb. and 4 lbs., preferably between 2½ lbs. and 3 lbs., is applied to separate the coupling 146 from the bag drainage tube 16, the riser assembly 94" and the spring clamp assembly 91' will separate from one another so that the splined shaft 89 is pulled out of the duckbill valve 86' and valve opener risers 94' of the riser assembly 94" will disengage from the valve leaflets 88" of the umbrella valve assembly 88'. Thus, the duckbill valve 86' will close and the umbrella valve assembly 88' will close so as to respectively prevent fluid discharge from the bag drainage tube 16 and the catheter drainage tube 10 attached to the coupling 146.

Basically, the calibrated disconnect joint for urethral catheters of this invention provides an in-line quick release connector. This connector can be placed at a junction between a catheter-drainage tube and a bag-drainage tube or it may be built into the catheter-drainage tube or the bag-drainage tube. A "built-in" system would probably be best if the calibrated disconnect joint were located at a neck of the enlarged terminal funnel portion 14 (FIG. 1) so as to form a drainage tubing adaptor, such as adaptor 44 shown in FIG. 2. In this position, the calibrated separation can take place downstream of the fork 35 so that the inflation pigtail 74 can act as a deterrent to possible migration of the catheter-drainage tube once it has separated from the bag-drainage tube.

Furthermore, a calibrated disconnect joint of this invention is small, easy to use, and can be readily adapted to both existing catheter-drainage tubes and bag-drainage tubes.

It should be particularly noted that in most of the preferred embodiments, one of the tubular members forming the calibrated disconnect joint is made of medical grade polyethylene, which contains inherently different plasticizers than the latex or silicon which is normally used to form the bag-drainage tube and the catheter-drainage tube. Different plasticizers are important, because it is necessary to prevent the exchange of plasticizers between joint members which form a bacteria-free joint. If the drainage-tubes and the in-line member of the calibrated disconnect joint, which is constructed of polyethylene, were made of similar materials, they would tend to adhere to each other, which would, over time, randomly increase the separation force required to disconnect the parts. This would make the separation force required unpredictable so that it might be moved outside of tolerance limits and would therefore reduce the product's potential efficacy.

In any event, those of ordinary skill in the art will realize that the calibrated disconnect joint of this invention provides an inexpensive safety feature to urinary catheters which prevents unnecessary suffering and injury to patients.

The embodiments of the invention in which an exclusive property or privilege are claimed are defined as follows:

1. A calibrated disconnect joint for use with indwelling urethral balloon catheters, said calibrated disconnect joint comprising:

a first tubularly-shaped wall member defining a lumen, said tubularly-shaped wall member including a first strong attachment means positioned at a distal end thereof for providing a strong attachment of said first tubularly-shaped wall to said catheter-drainage tube requiring a force greater than 6 pounds axial pull to separate said first tubularly-shaped wall from said catheter-drainage tube, said first tubularly-shaped wall member including a first calibrated connector at a proximal end thereof;

a second tubularly-shaped wall member including a second strong attachment means positioned at a proximal end thereof for providing a strong attachment of said second tubularly-shaped wall to a bag-drainage tube requiring a force of greater than 6 pounds axial pull to separate said second tubularly-shaped wall member from said bag-drainage tube, said second tubularly-shaped wall including a second calibrated connector at a distal end thereof;

wherein one of said first and second tubularly-shaped wall members is a male connector and the other is a female connector, said male and female connectors telescoping together, and wherein said male and female connectors include means for interengaging said connectors with one another to form a sealed coupling which automatically separates said connectors upon receiving a separating tension of between ½ and 6 pounds.

2. A calibrated disconnect joint as in claim 1 wherein said first tubularly-shaped wall member is formed as a separate piece from said catheter-drainage tube.

3. A calibrated disconnect joint as in claim 2 wherein said second tubularly-shaped wall member is formed as a separate piece from said bag drainage tube.

4. A calibrated disconnect joint as in claim 3 wherein one of said connectors defines an indented groove and the other of said connector comprises an annularly-shaped rib for mating with said groove.

5. A calibrated disconnect joint as in claim 1 wherein said second tubularly-shaped wall is formed as a separate piece from said bag-drainage tube.

6. A calibrated disconnect joint as in claim 1 wherein one of said connectors defines an annular groove and the other of said connectors comprises an outwardly-protruding annular rib for mating with said groove.

7. A calibrated disconnect joint as in claim 6 wherein said male connector formes an external surface having an outwardly-tapered conically-shaped external surface with said outwardly-protruding annularly-shaped rib being positioned thereon and said female connector comprises an internal surface which tapers inwardly toward an outer end thereof, with said groove being positioned at said taper for receiving said rib, with said external and internal surfaces contacting one another along the length thereof to form a bacteria-migration-free seal therebetween.

8. A calibrated disconnect joint as in claim 1 wherein means for interengaging said connectors forms a sealed coupling which automatically separates said connectors upon receiving a separating tension of around 2½-3 pounds.

9. A calibrated disconnect joint as in claim 8 wherein is further included a valve in each of said first and second tubularly-shaped wall members for preventing fluid from flowing from said first and second tubularly-shaped wall members at said valves if said first and second tubularly-shaped wall members are separated, but one of said first and second tubularly-shaped wall members including a means for engaging the valve mounted on the other of said tubularly-shaped wall members for maintaining the engaged valve in an open configuration so long as the tubularly-shaped wall members are not separated.

10. A calibrated disconnect joint as in claim 1 wherein one of said first and second tubularly-shaped wall members defines an opening thereinto with a membrane thereon to serve as a sampling/injection port.

11. A calibrated disconnect joint as in claim 1 wherein one of said first and second tubularly-shaped wall members defines an opening thereinto with a semipermeable membrane thereon to serve as an air vent.

12. A urethral catheter system comprising:
a catheter-drainage tube having a balloon on a distal end thereof;
a bag-drainage tube for being attached to a receptacle bag for receiving fluid passing through said catheter-drainage tube;
a calibrated disconnect joint for interconnecting said catheter-drainage tube and said bag-drainage tube, said calibrated tubular connector comprising:
a first tubularly-shaped wall member defining a lumen, said first tubularly-shaped wall member including a first strong attachment means positioned at a distal end thereof for providing a strong attachment of said first tubularly-shaped wall to said catheter-drainage tube requiring a force greater than 6 pounds axial pull to separate said first tubularly-shaped wall from said catheter-drainage tube, said first tubularly-shaped wall member including a first calibrated connector at a proximal end thereof;
a second tubularly-shaped wall member including a second strong attachment means positioned at a proximal end thereof for providing a strong attachment of said second tubularly-shaped wall to a bag-drainage requiring a force of greater than 6 pounds axial pull to separate said second tubularly-shaped wall member from said drainage-bag, said second tubularly-shaped wall including a second calibrated connector at a distal end thereof;
wherein one of said first and second tubularly-shaped wall members is a male connector and the other is a female connector, said male and female connectors telescoping together, and wherein said male and female connectors include means for interengaging said connectors with one another to form a sealed coupling which automatically separates upon receiving a separating tension of between ½ and 6 pounds.

13. A urethral catheter system as in claim 12 wherein said first tubularly-shaped wall member is formed as a separate piece from said catheter-drainage tube.

14. A urethral catheter system as in claim 13 wherein said second tubularly-shaped wall member is formed as a separate piece from said bag drainage tube.

15. A urethral catheter system as in claim 14 wherein one of said connectors defines an indented groove and the other of said connectors comprises an annularly-shaped rib for mating with said groove.

16. A urethral catheter system as in claim 12 wherein said second tubularly-shaped wall member is formed as a separate piece from said bag drainage tube.

17. A urethral catheter system as in claim 12 wherein one of said connectors comprises an annular groove and the other of said connectors comprises an outwardly-protruding annular rib for mating with said groove.

18. A urethral catheter system as in claim 17 wherein said male connector forms an external surface having an outwardly-tapered conically-shaped with said outwardly-protruding annularly-shaped rib being positioned thereon and said female connector comprises an internal surface which tapers inwardly toward an outer end thereof, with said groove being positioned at said taper for receiving said rib, with said external and internal surfaces contacting one another along the length thereof to form a bacteria-migration-free seal therebetween.

19. A urethral catheter system as in claim 12 wherein said connectors automatically separate upon receiving a separating tension of around 2½-3 pounds.

20. A urethral catheter system as in claim 19 wherein is further included a valve in each of said first and second tubularly-shaped wall members for preventing fluid from flowing from said first and second tubularly-shaped wall members at said valves if said first and second tubularly-shaped wall members are separated, but one of said first and second tubularly-shaped wall members including a means for engaging the valve mounted on the other of said tubularly-shaped wall members for maintaining the engaged valve in an open configuration so long as the tubularly-shaped wall members are not separated.

21. A method of protecting patients using urethral catheter systems comprising catheter-drainage tubes which are held inside of patients by balloons and bag-drainage tubes which are connected to the catheter-drainage tubes external of the patients for channelling fluid passing through the catheter-drainage tubes into retainer bags comprising the step of:
placing a calibrated disconnect joint at the interconnection between the catheter-drainage tube and the bag-drainage tube which automatically disconnects when a separating axial force of between ½ and 6 pounds is applied thereto.

22. A method as in claim 21 where the separating axial force is between around 2½ and 3 pounds.

23. A catheter joint for use with a catheter, said catheter joint comprising:

an elongated tubular housing defining a side port;
a hydrophobic filter mounted in said side port for allowing ventilation to an interior passage of said catheter; and
a membrane also mounted in said side port for allowing a sampling of fluid material in the interior passage of said catheter with a needle passed therethrough without unduly exposing the interior passage of the catheter to outside atmosphere.

24. A catheter joint as in claim 23 wherein one of said hydrophobic filter and membrane has an annular shape so as to define a hole in the middle thereof and wherein the other is mounted in said hole.

25. A catheter joint as in claim 23 wherein is further included a fluid impervious cap for being selectively placed on said port for preventing passage of fluid through said port.

* * * * *